(12) United States Patent
Van Damme

(10) Patent No.: US 11,534,580 B2
(45) Date of Patent: Dec. 27, 2022

(54) FIXATION OF MEDICAL TUBING WITH FLUIDUM FILLED CHAMBER

(71) Applicant: BEDAL NV, Diepenbeek (BE)

(72) Inventor: Alexander Van Damme, Zoersel (BE)

(73) Assignee: BEDAL NV, Diepenbeek (BE)

(*) Notice: Subject to any disclaimer, the term of this patent is extended or adjusted under 35 U.S.C. 154(b) by 0 days.

(21) Appl. No.: 16/651,404

(22) PCT Filed: Oct. 1, 2018

(86) PCT No.: PCT/EP2018/076697
§ 371 (c)(1),
(2) Date: Mar. 27, 2020

(87) PCT Pub. No.: WO2019/063847
PCT Pub. Date: Apr. 4, 2019

(65) Prior Publication Data
US 2020/0297974 A1    Sep. 24, 2020

(30) Foreign Application Priority Data
Sep. 30, 2017  (EP) .................................. 17194271

(51) Int. Cl.
*A61M 25/02*    (2006.01)
(52) U.S. Cl.
CPC ....... *A61M 25/02* (2013.01); *A61M 2025/024* (2013.01); *A61M 2025/028* (2013.01);
(Continued)
(58) Field of Classification Search
CPC ............ A61M 25/02; A61M 2025/028; A61M 2025/024; A61M 2025/0246;
(Continued)

(56) References Cited

U.S. PATENT DOCUMENTS

| 4,897,082 A | 1/1990 | Erskine |
| 6,572,588 B1 * | 6/2003 | Bierman ............... A61M 25/02 |
| | | 604/174 |

(Continued)

FOREIGN PATENT DOCUMENTS

| DE | 3807944 A1 | 9/1989 |
| FR | 2517544 A1 | 6/1983 |

(Continued)

OTHER PUBLICATIONS

International Search Report in reference to co-pending European Patent Application No. PCT/EP2018/076697 filed Oct. 1, 2018.

*Primary Examiner* — James D Ponton
*Assistant Examiner* — Neeraja Gollamudi
(74) *Attorney, Agent, or Firm* — Dinsmore & Shohl, LLP

(57) ABSTRACT

A medical device (100) for securing a catheter (700) to a support (600) is described, comprising a base element (200) having a first side (201) fixable to the support (600), and a second side (202) opposite the first side (201), and comprising a top element (500) having a first side (501) connectable with the second side (202) of the base element (200). When the first side (501) of the top element (500) is connected with the second side (202) of the base element (200), the top element (500) and the base element (200) are arranged for forming a feedthrough for the catheter (700) between the second side (202) of the base element (200) and the first side (501) of the top element (500). At least one of the base element (200) and the top element (500) comprises a deformable fluidum filled chamber (430), the deformable fluidum filled chamber (430) arranged such that the catheter (700) is locally tightly held between the base element (200) and the top element (500) when positioned there between.

21 Claims, 4 Drawing Sheets

(52) U.S. Cl.
CPC ............ *A61M 2025/0246* (2013.01); *A61M 2025/0266* (2013.01); *A61M 2205/0216* (2013.01)

(58) Field of Classification Search
CPC .. A61M 2025/0266; A61M 2205/0216; A61M 2025/0273
See application file for complete search history.

(56) References Cited

U.S. PATENT DOCUMENTS

| | | | |
|---|---|---|---|
| 2006/0118117 A1* | 6/2006 | Berthon-Jones | ............................. A61M 16/0057 128/206.27 |
| 2006/0276752 A1* | 12/2006 | Bierman | ............... A61M 25/02 604/174 |
| 2010/0137807 A1 | 6/2010 | Kessler | |
| 2015/0224285 A1* | 8/2015 | Howell | ................. A61M 25/02 604/174 |
| 2016/0367789 A1* | 12/2016 | Beran | .................... A61M 25/02 |
| 2018/0207416 A1* | 7/2018 | Roddy | .................. A61M 25/02 |

FOREIGN PATENT DOCUMENTS

| | | |
|---|---|---|
| WO | 0168180 A1 | 9/2001 |
| WO | 2015086673 A1 | 6/2015 |

\* cited by examiner

FIXATION OF MEDICAL TUBING WITH FLUIDUM FILLED CHAMBER

TECHNICAL FIELD OF THE INVENTION

The present invention relates to catheters used in healthcare and in particular to fixing such catheters to a support.

BACKGROUND OF THE INVENTION

In healthcare, a catheter is used to provide an access to the human body for drainage of a bodily fluid or for delivery of medicinal drugs, parenteral nutrition, blood or blood components or other liquids. A catheter is typically used for patients that are ill or during the performance of surgical procedures. Depending on the type of liquid that needs to be delivered or evacuated and sometimes also depending on the patient or his/her medical condition, different catheters and different methods of applying them can be selected.

A first type of catheter is the peripheral venous catheter. This catheter is inserted in a peripheral vein. A second type of catheter is a midline catheter. Such a catheter typically is between 8 and 25 cm long and is often placed in an upper arm vein. A third type of catheter is a central venous catheter which is placed into a large vein. A fourth type of catheter is a drainage catheter for draining bodily fluids from the body, such as for example but not limited to a bladder catheter.

Still other types of catheters are peripherally inserted central catheters, tunnelled catheters and port catheters. These catheters can be applied at several places on the human body, such as for example in the breast area of a patient.

A large number of patients needs to make use of catheters, such as for example central catheters, tunnelled catheters or port catheters, for a long period, e.g. weeks or months. It often is preferred to make use of a same catheter for a longer time period, as correctly positioning a catheter is time consuming and as replacing or re-introducing a catheter into the human body typically results in additional risks for infections and additional pain for the patient during installing.

A disadvantage of the use of a catheter is that it often limits the patient in actions they can take. For example, excessive movement (e.g. for washing or taking a shower) whilst a catheter or part thereof is applied to the human body may be difficult or impossible as the position of the catheter within the body should under all circumstances remain fixed. A change in position of the catheter may prevent proper operation and, in some circumstances, could even lead to dangerous or life threatening situations. Furthermore, it should be avoided that dirt, air or shower water enters the catheter, which may more readily occur when the catheter isn't properly secured. In order to avoid such critical situations, often these actions are prohibited for patients having a catheter applied. Adequate fixation could prevent critical situations and could allow for these movements to be performed in safety.

Known medical devices for securing catheters are sold by Statlock®. However, these medical devices are suited only for one catheter diameter, or for a limited range thereof, such that several different types of the medical device need to be purchased and used for different catheters.

There is thus still a need in the art for a means for securing a catheter which addresses some or all of the issues outlined above.

SUMMARY OF THE INVENTION

It is an object of the present invention to provide good means for securing a catheter to a support. This objective is accomplished by a device and a use according to the present invention.

It is an advantage of embodiments of the present invention that a catheter can be well secured with little or no loss of flow rate through the catheter (e.g. without pinching the catheter).

It is an advantage of embodiments of the present invention that the medical device can receive catheters of varying diameters.

It is an advantage of embodiments of the present invention that a catheter can be secured to a living creature or to an inanimate object.

It is an advantage of embodiments of the present invention that the medical device may conform to the support. It is a further advantage of embodiments of the present invention that a considerable level of user comfort can be achieved.

In a first aspect, the present invention relates to a medical device for securing a catheter to a support, comprising a base element having a first side fixable to the support and a second side opposite the first side, and comprising a top element having a first side connectable with the second side of the base element. When the first side of the top element is connected with the second side of the base element, the top element and the base element are arranged for forming a feedthrough for the catheter between the second side of the base element and the first side of the top element. Furthermore at least one of the base element and the top element comprises a deformable fluidum filled chamber and the deformable fluidum filled chamber is arranged such that, when the first side of the top element is connected with the second side of the base element, the catheter is, by deformation of the fluidum filled chamber, locally tightly held between the base element and the top element when positioned therebetween.

In a second aspect, the present invention relates to a use of the medical device as defined in any embodiment of the present invention for securing the catheter to the support.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
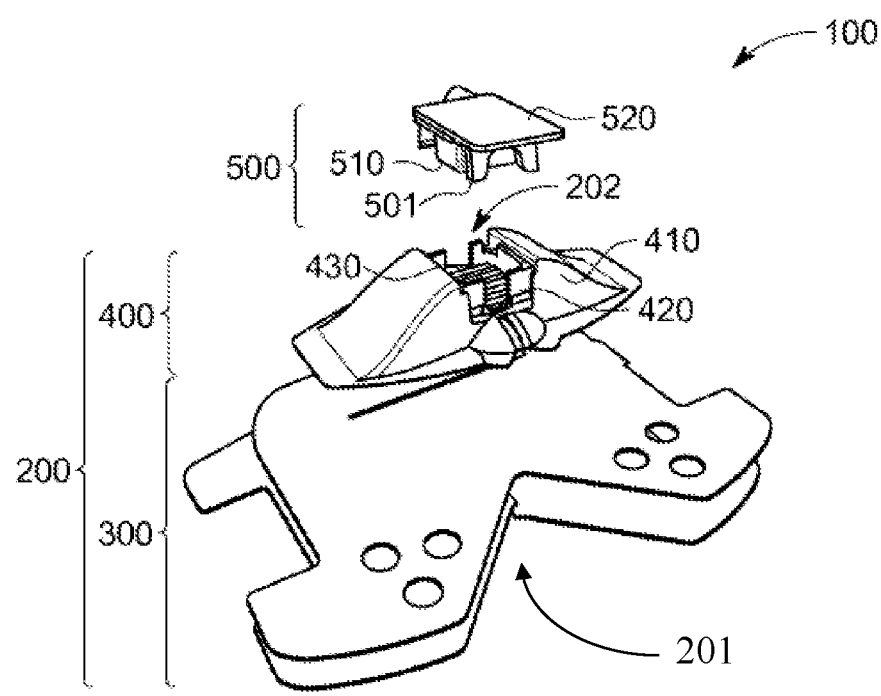
FIG. 1 is an exploded view of a first and second portion of a base element, and a top element, according to an embodiment of the present invention.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "coupled", also used in the claims, should not be interpreted as being restricted to direct connections only. The terms "coupled" and "connected", along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices or means. "Coupled" may mean that two or more elements are either in direct physical, or that two or more elements are not in direct contact with each other but yet still co-operate or interact with each other.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention.

As used herein, and unless otherwise specified, when a medical device is said to secure a catheter to a support, it is meant that at least a portion of the catheter is fixed to and/or stabilized to and/or positioned onto the support. Securing the catheter typically hinders, or even completely prevents, both translational and rotational movement of at least the portion of the catheter.

In a first aspect, the present invention relates to a medical device for securing a catheter to a support. The catheter may be for example a drainage catheter, a central venous catheter, a peripheral venous catheter, a midline catheter, a tunnelled catheter, a port catheter or a dialysis catheter. The medical device can advantageously be used in a plurality of applications.

In embodiments, the support may be a body of a living creature. Securing the catheter to the living body advantageously reduces the risk of the catheter moving within the body or even being accidentally removed therefrom. In other embodiments, the support may be an inanimate object, such as a bed or a standard. Securing the catheter to an inanimate object advantageously helps in guiding the catheter in a desired path, e.g. reducing the risk of inadvertently tripping over it.

The medical device for securing comprises a base element having a first side fixable to the support, e.g. living body, and a second side opposite the first side. It also comprises a top element having a first side connectable with the second side of the base element. According to embodiments of the present invention, when the first side of the top element is connected with the second side of the base element, the top element and the base element are arranged for forming a feedthrough for the catheter between the second side of the base element and the first side of the top element. Furthermore, at least one of the base element and the top element comprise a deformable fluidum filled chamber. The deformable fluidum filled chamber is arranged such that the catheter is, due to deformation of the fluidum filled chamber, locally tightly held between the base element and the top element when the catheter is positioned there between.

It was surprisingly found within the present invention that the use of the deformable fluidum filled chamber allow for a tight fixation of a catheter within the medical device, without causing pinching thereof. It was further surprisingly found that this deformable fluidum filled chamber can adapt to a relatively broad range of catheter diameters, thus eliminating the need to buy and use several devices dedicated to specific catheter diameters.

In embodiments, the feedthrough may be, in absence of the catheter, not pre-shaped according to the shape of a catheter to be received.

The fluidum filled chamber may be filled with air. In some embodiments, the fluidum filled chamber may be a closed chamber. The chamber may be filled with air or any other type of gas, or more generally with a fluidum.

In embodiments, the base element and/or the top element may comprise a rigid material arranged such that the deformable fluidum filled chamber is forced to at least partially engulf the catheter. The rigid material may advantageously guide the fluidum filled chamber to deform within an enclosed volume, thereby better engulfing the catheter and improving the fixation thereof within the medical device.

In embodiments, the first side of the top element may be connectable to the second side of the base element through a reversible connection mechanism. The reversible connection mechanism may for example comprise a click mechanism, a clip mechanism, etc. The reversible connection advantageously allows to easily lock the device, thereby securing the catheter, as well as easily unlock the device, in order to remove the catheter.

In embodiments, the top element and/or the base element may for example be adapted such that these comprises protrusions and/or indentations of the top element and/or the base element. These protrusions and/or indentations can be used for fixing the top element to the base element, thus forming the click or clip mechanism. These protrusions (e.g. 'teeth') can advantageously also form an additional fixation of the catheter, such as a physical barrier to avoid movement of the catheter upon exertion of a pulling force.

In embodiments, the base element may be adapted to conform to the support. In embodiments, a shape of the base element may be adapted to a shape of the support. The base element may be advantageously shaped to fit to the support, such as being shaped such that it is comfortable to the living being. This may include having a shape covering a relatively broad area, such that forces exerted on the medical device are spread out over the broad area. In embodiments, the base element may be flexible. The base element can advantageously adapt its shape to conform to the support, thereby for example being more comfortable to wear for the living being.

In embodiments, the first side of the base element may be fixable to the support by means of an adhesive material. The adhesive material advantageously allows the first side to be easily fixed to the support. In preferred embodiments, the fixation may be reversible, such as by using a removable adhesive. In other embodiments, the fixation may be permanent (e.g. being welded to an inanimate object) or semi-permanent (e.g. being bolted to an inanimate object).

In embodiments, the top element may be coupled e.g. permanently coupled, to the base element through a flexible tether. Coupling the top element to the base element with a flexible tether (e.g. a leash) advantageously prevents the top element from being easily dropped or lost. Furthermore, the tether may aid in the correct placement of the top element on the base element.

In embodiments, a portion of the catheter may be present between the base element and the support. An additional fixation of the catheter can advantageously be achieved by securing a portion of it between the base element and the support.

In embodiments, the base element may comprise an anti-kinking structure. The anti-kinking structures can advantageously guide the catheter at the exit points of the medical device and thereby help to avoid kinking of the catheter.

In some embodiments, the surfaces forming the feedthrough may show a certain structural roughness, although embodiments where the surfaces are substantially flat provide better fixation. The materials used may be materials with a high shear resistance, i.e. a high friction coefficient, resulting in a good grip thus a good fixation. The material used may be TPU, although embodiments are not limited thereto.

In embodiments, the base element and/or the top element may comprise a cavity for securing a winged catheter. Be providing cavities in which the wings of the winged catheter can be introduced, the fixation of the catheter that is achieved by the medical device can advantageously be improved.

In embodiments, the catheter may comprise multiple lumen. In embodiments, the medical device may be configured for securing the catheter at the split section. Being able to fix the catheter at the split section can be particularly advantageous as a fixation point for the plurality of ends can be achieved with a single medical device.

In embodiments, the at least one of the base element and/or the top element comprises a deformable fluidum filled chamber at each side of the tube of the catheter for locally tightly holding wings of a winged catheter. The deformable fluidum filled chamber may be at the upper side, i.e. at the top element, or at the bottom side, i.e. the base element, or both at the upper side and the bottom side. Furthermore, although in principle a deformable fluidum filled chamber also may be present only at one side of the tube (e.g. left or right for the left or right wing), typically wings will be present at both sides of the catheter so the presence of one or more deformable fluidum filled chamber(s) at each side of the catheter will be advantageous.

In embodiments, the medical device may further comprising a protective foil covering the base element and the top element. In preferred embodiments, the protective foil may be applied such that a watertight seal is formed with the support. The protective foil can advantageously be used to protect the fixation of the medical device, and an entry point of the catheter into the support if present nearby, from water, dust, etc. This can further allow the patient to perform certain actions which might otherwise be prohibited, such as washing or showering. Protective foils of this kind have been disclosed in EP3079753 A1, which is hereby incorporated herein by reference.

In a second aspect, the present invention relates to a use of the medical device as defined in any embodiment of the present invention for securing the catheter to the support.

In embodiments, any feature of the second aspect may be as correspondingly described for any embodiment of the first aspect.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

Example 1: Medical Device Securing a Catheter to a Support

We now refer to FIG. 1, showing an exploded view of a medical device 100 in accordance with the present invention. The medical device 100 comprises a base element 200 and a top element 500. In this example, the base element 200 comprises a first portion 300, comprising the first side 201, for securing the device 100 to the support (e.g. a body part). The first portion 300 may for example be flexible such that it can conform to the shape of the support and may be attached using an adhesive, e.g. a tape. The base element 200 further comprises a second portion 400, comprising the second side 202, for receiving therein a catheter. The second portion 400 is typically fixed to the first portion 300 and may comprise a soft material 410, which may at least partially conform to the support, and a rigid material 420, which aids in securing the catheter. The shape of the second portion 400 may furthermore be selected to better conform to the support, e.g. by being curved and/or by covering a somewhat larger surface. In this way, for example a better patient comfort can be achieved; e.g. when a patient lies on the medical device 100, the medical device 100 can deform to an extent and the force that is exerted can be divided over a broader surface, making the wearing of the device more comfortable. The second portion 400 further comprises a fluidum filled chamber 430, surrounded by the more rigid material 420, in the form of the soft material 410 enclosing a fluidum bubble. The fluidum filled chamber 430 can deform and partially envelop the catheter; this action is reinforced by the rigid material 420 which force the deformation to remain within the surrounded volume.

The medical device 100 also comprises a top element 500, comprising the first side 501. The top element 500 again comprises a rigid material 520 and a soft material 510. The soft material 510 can also comprise a fluidum bubble to form another fluidum filled chamber (not shown). These features of the top element act similarly and in conjunction with the corresponding features of the second portion 400 of the base element 200, thereby forming a feedthrough for the catheter (which can adapt to e.g. a diameter of the catheter) while nevertheless tightly holding it in place.

Figure 2:
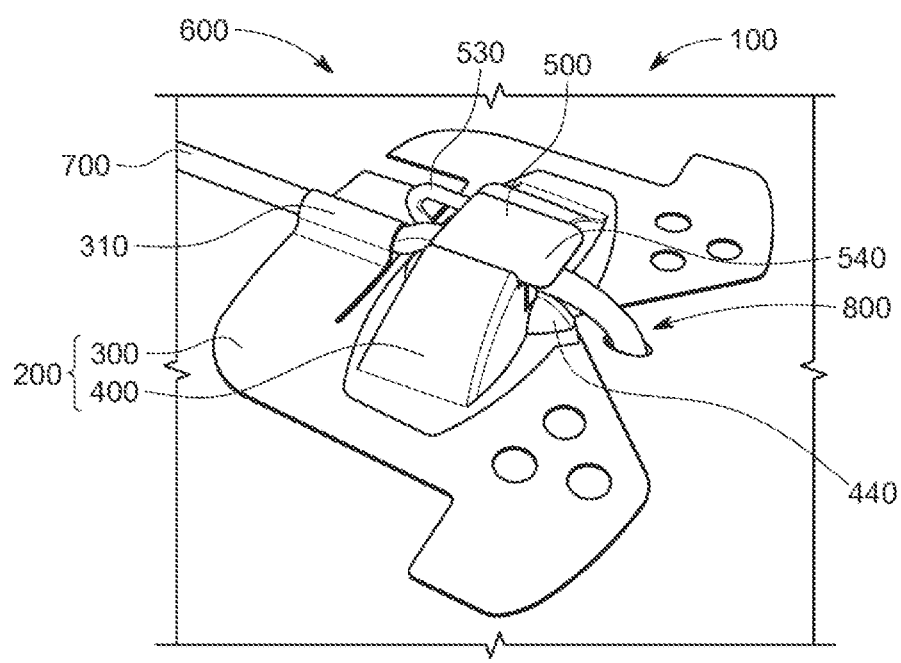
FIG. 2 is a schematic representation of a medical device securing a catheter to a support, according to an embodiment of the present invention.

We now refer to FIG. 2, showing a medical device 100 securing a catheter 700 to a support 600. The first portion 300 of the base element 200 is attached to the support 600. The catheter 700 is tightly held between the second portion 400 of the base element 200 and the top element 500 thanks to the fluidum filled chamber which engulfs the catheter 700. Furthermore, the flow rate of the catheter 700 is not or barely reduced, because the fluidum filled chamber deforms around the catheter 700 without pinching it shut. As shown in FIG. 2, the medical device 100 can be secured close to an entry point 800 of the catheter 700 in the support 600. The first portion 300 is shaped such that the entry point 800 is visible for inspection. The first portion 300 is also configured such that a portion 310 of it overlays the catheter 700, providing an additional fixation of the catheter 700 to the support 600. The medical device 100 is further configured with anti-kinking structures 440 which guide the catheter 700 and which prevent kinking thereof. In order to facilitate handling, the top element 500 is coupled to the base element 300 using a tether 530, prevent the top element 500 from being dropped while connecting the different elements and aiding in the correct positioning of said top element 500. The top element 500 is designed to allow easy opening and closing of the medical device 100. To this end, it comprises a lip 540 that facilitates operating it with a finger. The top element 500 can further be shaped with an incision in its top part, allowing movement of a top arch and facilitating opening and closing of the medical device 100.

Example 2: Use of a Protective Foil with the Medical Device

Figure 3:
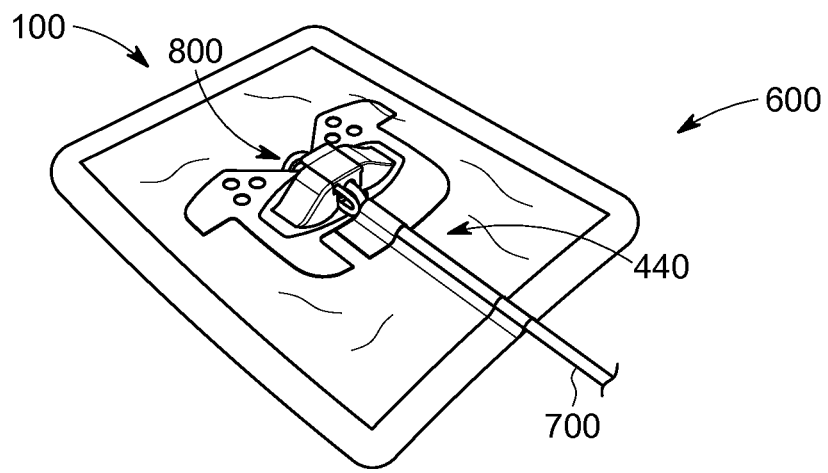
FIG. 3 is a schematic representation of protective foil covering a medical device securing a catheter, according to an embodiment of the present invention.

We now refer to FIG. 3, showing a medical device 100, as described in example 1, covered by a protective foil 800. The protective foil 800 may for example be a flexible and stretchable foil (e.g. from plastic material), at least the sides of which can be attached (e.g. using an adhesive) to the support 600 (e.g. a body part). Preferably, the protective foil 800 may be a watertight foil that is attached in such a way that a watertight seal is formed between the protective foil 800 and the support 600. The protective foil 800 can thus be used to protect the medical device 100 and a portion of catheter 700 from water, dust, etc. This may be particularly useful when the medical device 100 is located next to the entry point 800 of the catheter 700 into the living being 600, as the protective foil 800 may in that case also prevent water, dust, etc. from entering into the body 600 through that opening 800. This can for example enable the person to wash without danger of e.g. water entering the catheter 700 or the body. Additional comfort and security can be achieved by using for the foil a highly breathable material with a high tear and puncture resistance.

Figure 4:
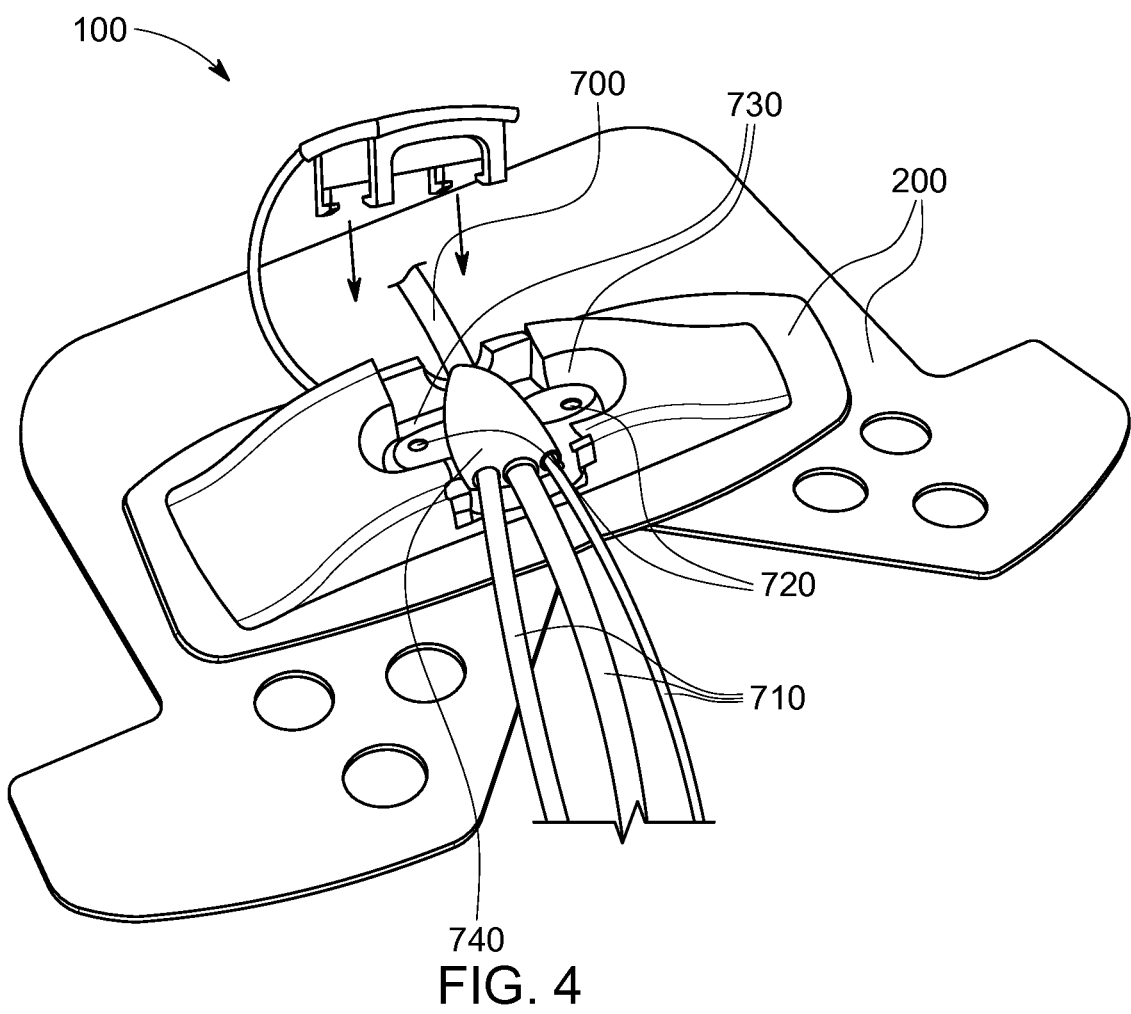
FIG. 4 is a schematic representation of a medical device adapted for securing a winged catheter comprising multiple lumen, according to an embodiment of the present invention.

Example 3: Medical Device for Securing a Winged Catheter Comprising Multiple Lumen We now refer to FIG. 4, showing a medical device 100 and a catheter 700 having one end splitting into three lumen 710; the base element 200 of the medical device 100 being configured to allow room for these lumen.

Figure 5:
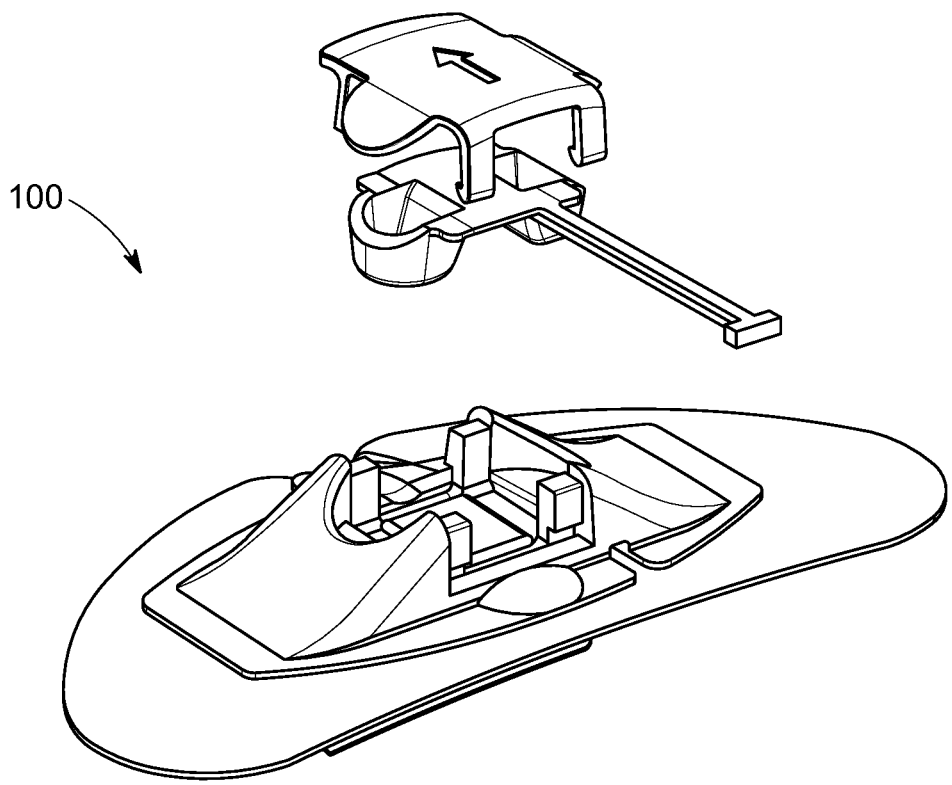
FIG. 5 is another example of a medical device adapted for securing a winged catheter, according to an embodiment of the present invention.
Figure 6:
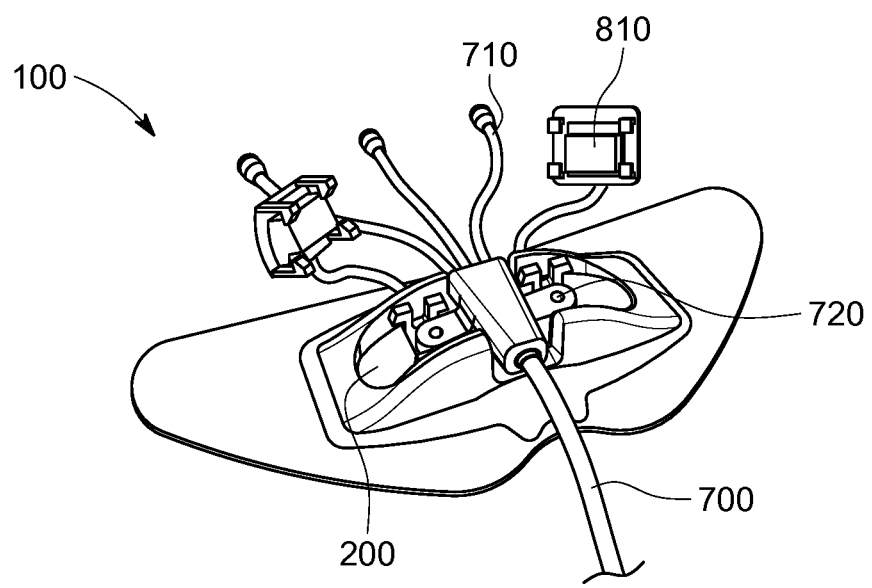
FIG. 6 and FIG. 7 illustrate an open and closed state of a medical device adapted for securing a winged catheter, according to an embodiment of the present invention.
Figure 7:
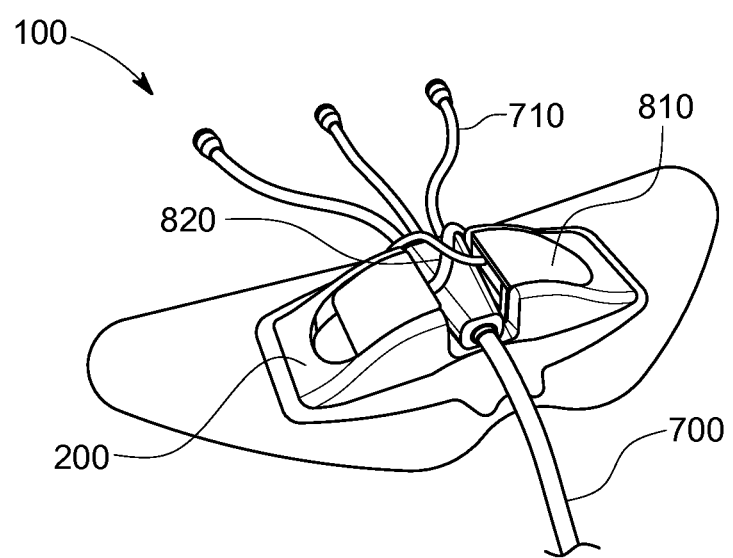

Furthermore, the catheter 700 comprises two wings 720 at the split portion and the medical device 100 comprises the adaptation of having two cavities 730 in the base element 200 for receiving the two wings 720 therein. In this way the medical device 100 can be used to stabilize the catheter 700 at the split portion 740. In FIG. 5, another example is shown whereby the medical device 100 is adapted for fixing wings provided at the side of the tube of the catheter. The medical device 100 comprises two deformable fluidum filled chambers for tightly holding the wings attached to the tube. An additional fluidum filled chamber can be provided at a central position to also tightly hold the tube, although it may be sufficient to fix the wings in order to sufficiently fix the catheter. In the example of FIG. 5, the top portion is a portion that is applied centrally with a single snapping or clicking action. A further example illustrating a medical device 100 for fixating a winged catheter 700 is shown in FIG. 6 and FIG. 7. FIG. 6 illustrates the medical device 100 in an open position (the top portion not being snapped or clicked), whereas FIG. 7 illustrates the medical device 100 in a closed position (the top portion being snapped or clicked to the base portion). The medical device 100 is for example suitable for fixing a catheter 700 with wings 720, the catheter 700 in the example shown is being split in three lumen 710. In the present example, the top portion of the medical device is split in two parts 810, each part 810 snapped or clicked over one of the wings 720. By splitting the top portion, the medical device 100 can be made small and with a limited height, resulting in improved comfort for the user. In the medical device, the two parts 810 of the top portion are connected to the base portion 200 by leashes 820, whereby, when the two parts 810 are snapped or clicked on the base portion, the leashes 820 cross over the tube 700 and additionally assist in fixing the tube 700.

By way of illustration, embodiments of the present invention not being limited thereto, the devices were tested with respect to their fixation properties and the effect of fixation on the flow through the catheters. It was found that the medical devices were able to firmly fix the catheters so that neither translation, nor rotation occurred substantially, while the flow through the catheters was not or only very limited reduced. The latter therefore confirmed the excellent securing properties of the medical devices.

It is to be understood that although preferred embodiments, specific constructions and configurations, as well as materials, have been discussed herein for devices according to the present invention, various changes or modifications in form and detail may be made without departing from the scope and technical teachings of this invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A medical device for securing a catheter to a support, the medical device comprising:
    a base element, the base element comprising a first side fixable to the support, and a second side opposite the first side; and
    a top element, the top element comprising a first side connectable with the second side of the base element,
    wherein:
        when the first side of the top element is connected with the second side of the base element, the top element and the base element are arranged for forming a feedthrough for the catheter between the second side of the base element and the first side of the top element;
        at least one of the base element and the top element comprise a deformable chamber, exclusively filled with air or any other type of gas, the deformable chamber arranged such that, when the first side of the top element is connected with the second side of the base element, the catheter is locally tightly held between the base element and the top element when positioned therebetween;
        the base element, or the top element, or both the base element and the top element, comprises a rigid material that guides the deformable chamber to deform within an enclosed volume which surrounds all sides of the deformable chamber, such that the deformable chamber is fully enclosed and forced to at least partially engulf the catheter; and
        the medical device is configured to secure catheters having a range of diameters.

2. The medical device according to claim 1, wherein the support is a body of a living creature.

3. The medical device according to claim 1, wherein the feedthrough, in absence of the catheter, is not pre-shaped with respect to a shape of a catheter to be received.

4. The medical device according to claim 1, wherein at least one of the base element and the top element comprises two deformable chambers at each side of a tube of a winged catheter for locally tightly holding wings of the winged catheter.

5. The medical device according to claim 4, wherein each of the base element and the top element comprise two deformable chambers at each side of a tube of a winged catheter for locally tightly holding wings of the winged catheter.

6. The medical device according to claim 1, wherein the base element is adapted to conform to the support.

7. The medical device according to claim 6, wherein a shape of the base element is adapted to a shape of the support.

8. The medical device according to claim 7, wherein the base element is flexible.

9. The medical device according to claim 6, wherein the base element is flexible.

10. The medical device according to claim 1, wherein the first side of the base element is fixable to the support with an adhesive material.

11. The medical device according to claim 1, wherein the top element is permanently coupled to the base element through a flexible tether.

12. The medical device according to claim 1, wherein a portion of the catheter is present between the base element and the support.

13. The medical device according to claim 1, wherein the base element comprises an anti-kinking structure.

14. The medical device according to claim 1, wherein the base element, the top element, or both the base element and the top element, comprise a cavity for securing a winged catheter.

15. The medical device according to claim 14, wherein the catheter comprises multiple lumens.

16. The medical device according to claim 1, wherein the catheter comprises multiple lumens.

17. The medical device according to claim 1, wherein the catheter is a drainage catheter, a central venous catheter, or a dialysis catheter.

18. The medical device according to claim 1, further comprising a protective foil covering the base element and the top element.

19. The medical device according to claim 1, wherein both the base element and the top element comprise the rigid material that guides the chamber to deform within the enclosed volume.

20. A method of securing a catheter to a support, the method comprising:
    fixing a medical device to the support; and
    securing the catheter to the medical device, wherein:
the medical device comprises:
a base element, the base element comprising a first side fixable to the support, and a second side opposite the first side; and
a top element, the top element comprising a first side connectable with the second side of the base element;
when the first side of the top element is connected with the second side of the base element, the top element and the base element are arranged for forming a feedthrough for the catheter between the second side of the base element and the first side of the top element, and
at least one of the base element and the top element comprise a deformable chamber, exclusively filled with air or any other type of gas, the deformable chamber arranged such that, when the first side of the top element is connected with the second side of the base element, the catheter is locally tightly held between the base element and the top element when positioned therebetween;
the base element, or the top element, or both the base element and the top element, comprises a rigid material that guides the deformable chamber to deform within an enclosed volume which surrounds all sides of the deformable chamber, arranged such that the deformable chamber is fully enclosed and forced to at least partially engulf the catheter; and
the medical device is configured to secure catheters having a range of diameters.

21. The method according to claim 20, wherein both the base element and the top element comprise the rigid material that guides the chamber to deform within the enclosed volume.

* * * * *